United States Patent
Kulkarni et al.

(10) Patent No.: US 7,704,725 B2
(45) Date of Patent: Apr. 27, 2010

(54) **PROCESS FOR THE PRODUCTION OF MACROLIDES USING A NOVEL STRAIN, *STREPTOMYCES* SP. BICC 7522**

(75) Inventors: Madhav Kulkarni, Bangalore (IN); Surekha K. Prabhu, Karnataka (IN); Madenahally Channabasappa Shivakumar, Karnataka (IN); Prijyajit Sengupta, Karnataka (IN); Sanjay Tiwari, Karnataka (IN); Rakesh Mendhe, Karnataka (IN); Nitin Patil, Karnataka (IN); Laxmi Adhikary, Karnataka (IN); Anand Khedkar, Karnataka (IN); Ramakrishnan Melarkode, Karnataka (IN); Ramavana Gururaja, Karnataka (IN); Shrikumar Suryanarayan, Karnataka (IN)

(73) Assignee: Biocon Limited, Karnataka (IN)

( * ) Notice: Subject to any disclaimer, the term of this patent is extended or adjusted under 35 U.S.C. 154(b) by 100 days.

(21) Appl. No.: 11/578,108

(22) PCT Filed: Apr. 12, 2004

(86) PCT No.: PCT/IN2004/000099

§ 371 (c)(1),
(2), (4) Date: Mar. 5, 2008

(87) PCT Pub. No.: WO2005/098011

PCT Pub. Date: Oct. 20, 2005

(65) Prior Publication Data

US 2008/0286842 A1      Nov. 20, 2008

(51) Int. Cl.
| | | |
|---|---|---|
| *C12P 17/00* | (2006.01) | |
| *C12P 17/16* | (2006.01) | |
| *C12N 1/20* | (2006.01) | |
| *C12N 15/00* | (2006.01) | |

(52) U.S. Cl. .................. 435/252.35; 435/117; 435/118; 435/440

(58) Field of Classification Search .................. None
See application file for complete search history.

(56) References Cited

FOREIGN PATENT DOCUMENTS

| | | |
|---|---|---|
| EP | 0184162 | 4/1994 |
| WO | WO 03068980 | 8/2003 |

OTHER PUBLICATIONS

Soeda, Shinsuke et al., "Studies on the Development of Tacrolimus Production-Monograph"; Seibutsu Kogaku Kaishi (1998, 76(9), 389-397.

*Primary Examiner*—Christian L Fronda
(74) *Attorney, Agent, or Firm*—Marjama Muldoon Blasiak & Sullivan LLP

(57) ABSTRACT

The present invention discloses a new strain of *Streptomyces* sp. BICC 7522, its variants or mutants and use of the strain for the production of macrolides, process of production and purification of microlides.

1 Claim, No Drawings

PROCESS FOR THE PRODUCTION OF MACROLIDES USING A NOVEL STRAIN, STREPTOMYCES SP. BICC 7522

FIELD OF THE INVENTION

The present invention relates to a new strain of *Streptomyces* sp. BICC 7522, its mutants or variants and use of the strain for the production of macrolides.

BACKGROUND OF THE INVENTION

In 1975, Vezina et al., identified (3S,6R,7E,9R,10R,12R, 14S,15E,17E,19E,21S,23S,26R,27R,34aS)-9,10,12,13,14, 21,22,23,24,25,26,27,32,33,34,34a-Hexadecahydro-9,27-dihydroxy-3-[(1R)-2-[(1S,3R,4R)-4-hydroxy-3-methoxycyclohexyl]-1-methylethyl]-10,21-dimethoxy-6,8, 12,14,20,26-hexamethyl-23,27-epoxy-3H-pyrido[2,1-c][1, 4]oxaazacyclohentriacontine-1,5,11,28,29(4H,6H,31H)-pentone, also known by the synonyms rapamycin and sirolimus as an antifungal antibiotic harvested from a *Streptomyces hygroscopicus* culture, which was isolated from an Easter Island soil sample. (*J. Antibiot.* 28, 721-726 (1975); and U.S. Pat. No. 3,929,992, was issued to Sehgal, et, al. Dec. 30, 1975). Martel R. et al. (1977) described the ability of this compound to inhibit the immune response (*Can. J. Physiol. Pharmacol*, 55, 48-51). More recently, Calne, R. Y. et al. (1989), has described rapamycin to be immunosuppressive in rats given heterotopic heart allografts. (*Lancet* vol. 2, p, 227). A compound, 15,19-Epoxy-3H-pyrido[2,1-c][1,4]oxaazacyclotricosine-1,7,20,21(4H,23H)-tetrone, 5,6,8,11,12,13,14, 15,16,17,18,19,24,25,26,26a-hexadecahydro-5,19-dihydroxy-3-[(1E)-2-[(1R,3R,4R)-4-hydroxy-3-methoxycyclohexyl]-methyl ethenyl]-14,16-dimethoxy-4, 10,12,18-tetramethyl-8-(2-propenyl)-, (3S,4R,5S,8R,9E, 12S,14S,15R,16S,18R,19R,26aS), also known by the synonyms FK506 and Tacrolimus disclosed by EP 184162 and U.S. Pat. No. 4,894,366 is also useful as immunosuppressant. Another compound, 15,19-Epoxy-3H-pyrido[2,1-c][1,4]oxaazacyclotricosine-1,7,20,21(4H,23H)-tetrone,8-ethyl-5,6, 8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-14,16-dimethoxy-4, 10,12,18-tetramethyl-, (3S,4R,5S,8R,9E,12S,14S,15R,16S, 18R,19R,26aS)-, also known by the synonyms Ascomycin, Immunomycin and FK 520, which is 17-ethyl analog of Tacrolimus, disclosed in EPO Publication No. 0184162 is also useful as an immunosuppressant.

Many other derivatives of these compounds as well as structural analogues have immunosuppressant property.

Many other derivatives or analogs of these compounds are known, which have antibiotic and/or immunosuppressant activity.

These agents inhibit the proliferative response of lymphocytes to alloantigen stimulation, and a variety of T cell associated immune reaction. The compounds suppress immune responses in vivo as well as in vitro and are highly potent. The immunosuppressive action of the compound is applicable in organ transplantation.

EP 0 184 162 disclosed production of Tacrolimus by submerged fermentation from *Streptomyces tsukubaensis*.

EP 0 184 162 also discloses production of immunomycin by submerged fermentation from *Streptomyces tsukubaensis* or *Streptomyces hygroscopicus*.

*Streptomyces hygroscopicus* is also known to produce sirolimus.

The present invention discloses a new strain of *Streptomyces* sp. BICC 7522, its variants or mutants and use of the strain for the production of macrolides.

SUMMARY OF THE INVENTION

The present invention related to a new strain of *Streptomyces* sp. BICC 7522, its variants or mutants. The present invention is also related to use of the new strain for the production of macrolides. Accordingly the present invention provides a) a new strain of *Streptomyces* b) variants of the new strain of *Streptomyces* c) mutants of the new strain *Streptomyces* d) a process for the production of macrolides comprising
   i) Fermentation of a new *Streptomyces* sp., its variant or mutant
   ii) Isolation and purification of macrolides.

The process of present invention has the following advantages;

1. higher productivity by the new strain 2. easy isolation of the product from the fermentation broth 3. very high product purity 4. economically attractive 5. industrially viable

DETAILED DESCRIPTION OF THE INVENTION

The first embodiment of the present invention is a new isolated and purified strain of *Streptomyces* sp. BICC 7522.

The second embodiment of the present invention is variants of the new strain.

The third embodiment of the present invention is mutants of the new strain. The mutants of the new strain can be obtained by classical mutagenesis or recombinant techniques.

The fourth embodiment of the invention is use of the *Streptomyces*, its variant or mutant for the production of macrolides. The new strain of *Streptomyces* can be used to produce macrolides comprising but not limiting to Tacrolimus, immunomycin, sirolimus or their analogs.

The fifth embodiment of the invention is the process of purification of the macrolides.

Isolation and Purification of the Strain

An actinomycete colony was isolated from soil sample procured from Dona Paula, Goa, India. 5 g soil with was weighed in conical flask and 50 ml of water was added and the contents were swirled for 15-30 seconds and allowed to settle. The supernatant was double filtered with coarse filter paper to get a clear suspension. Supernatant of soil sample collected above was passed through filtration assembly under vacuum, which housed 0.2-micron filter.

The filter was incubated onto Soyabean Casein Digest medium for several days to permit organisms to grow through the filter and into the agar surface. Bacterial colonies remained on the filter surface while actinomycetes grew through the filter onto the agar surface. The filter was removed after this initial growth period and following further incubation an actinomycete colony was found on the agar surface. The pin point colony appeared small, white, powdery with irregular margins. The culture was further enriched by streaking it onto the following medium. The plates were incubated at 30° C. for 10 days,

| | |
|---|---|
| Glucose - | 5 g |
| L-glutamic acid - | 4 g |
| KH2PO4 - | 1 g |
| NaCl - | 1 g |
| MgSO4•7H2O - | 0.7 g |
| FeSO4•7H2O - | 3 mg |
| Water - | 1 L |
| Agar - | 25 g |

The actinomycete thus isolated was purified, enriched and accessioned into Biocon Culture Collection as BICC 7522

Identification of the Strain 16S rDNA sequence showed 98.2% homology with *Streptomyces cinnamoneus* subsp. Ianosus and *Streptomyces cinnamoneus* subsp. sparsus.

By Riboprint pattern, BICC 7522 could neither be assigned to *S. cinnamoneus* subsp. Ianosus nor to *Streptomyces cinnamoneus* subsp. sparsus.

Physiological tests identified BICC 7522 as a member of *Streptomyces lavendulae* cluster with a correlation factor of 97.6 which is below the 98.9 which is required for species identification.

According to EP 0 184 162, *Streptomyces tsukubaensis* was considered related to *Streptomyces aburaviensis*, which belong to the *Streptomyces lavendulae* cluster.

Thus these three data suggests that *Streptomyces* sp. BICC 7522 is not related to *Streptomyces tsukubaensis*.

The next choice was *S. griseocarneum* cluster to which *S. cinnamoneum* is found with its subspecies.

Fatty acid pattern appears to be similar to *S. halstedii*, which does not belong to the *S. griseocarneum* cluster.

BICC 7522 matched with many of the ISP (International *Streptomyces* Project) markers with *S. cinnamoneus* but the most important diagnostic marker of this group verticillate composition of the spore chain could not be detected because BICC 7522 did not sporulate.

Based on 16S rDNA sequence, riboprint data, morphological, physiological and chemotaxonomical tests results, one can conclude BICC 7522 is closely related to the *S. griseocarneum/S. lavendulae* taxon but a definite species identification could not be obtained. *S. tsukubaensis* does not utilize starch and mannitol whereas BICC 7522 is capable of doing both.

It is clear from the identification that BICC 7522 is not related to *S. tsukubaensis*.

DNA-DNA Hybridization

The DNA-DNA similarity values are below the threshold value of 70% for the definition of bacterial species and do not indicate the relationship at the species level of strain BICC 7522 to the type strains of *Streptomyces cinnamoneus* subsp. *Ianosus* or *Streptomyces cinnamoneus* subsp, sparsus.

Thus, BICC 7522 is a new species of *Streptomyces*.

It has been deposited at the Microbial Type Culture Collection, Chandigarh, INDIA on Mar. 15, 2004 with the Accession No. MTCC 5144 under the Budapest Treaty.

Fermentation for the Production of Macrolide

The inoculum used for the seed can be a vegetative mycelium. The pH of said seed medium can be 6 to 7.5 before sterilization. The seed medium can be incubated at 25 to 35° C. for 40-55 hr. The said production medium can be at pH of 6 to 7.5 before sterilization. The said production medium can be Incubated at 24-35° C. for 148 to 300 hr.

Isolation and Purification of the Product

The product can be isolated and purified from the fermentation broth or any aqueous solution by any, combination or all of steps in any order described hereunder.

The aqueous phase containing the product can be extracted into water immiscible organic solvent. The water immiscible organic solvent is selected one or more among ethyl acetate, butyl acetate, toluene, butanol etc. Optionally, an organic phase containing product can be partially concentrated using suitable techniques. The organic phase can be chilled, preferably to a temperature less than 4° C. The organic phase containing product can be treated with ammonia gas. Preferably, the ammonia gas is sparged through the organic phase. Surprisingly, it was found that some impurities precipitate with ammonia. The mixture can be filtered to isolate any precipitated impurities. The filtration can be carried out using celite as filter aid. The filtrate can be concentrated. The concentrate can be subjected to silica gel chromatography. The silica gel can be washed with a solvent. The product can be eluted with a solvent mixture. The fractions containing product can be pooled and concentrated. The concentrate can be dissolved in an organic solvent, preferably ethyl acetate. Optionally, the solution is treated with activated charcoal, filtered, concentrated and dissolved in an organic solvent. At low temperature, preferably at a temperature less than 4° C., an antisolvent can be added to the solution to effect crystallization of the product. The crystals can be filtered and dried. The crystals can be subjected to silica gel chromatography pretreated with silver nitrate. The product can be eluted with a solvent. The fractions containing product can be pooled and concentrated. The product can be crystallized as described above. The crystals can be filtered and dried. Product of pharmaceutically acceptable grade can be obtained by this method.

Alternately, the crystals obtained after the first silica gel chromatography can be subjected to reverse phase chromatography. The fractions containing product can be pooled and extracted with a water-immiscible organic solvent. The extract can be dried and concentrated. The product can be crystallized from ethyl acetate and hexane, as described above. The crystals can be filtered and dried. Product of pharmaceutically acceptable grade can be obtained by this method.

The solvent used for silica gel chromatography can be one or more among ethyl acetate, propyl acetate, butyl acetate, alkyl alcohols, chloroform, dichloromethane, hexane, heptane, iso-octane, petroleum ether, etc.

The solvent used for crystallization can be one or more among methyl acetate, ethyl acetate, propyl acetate, butyl acetate, acetonitrile, diethyl ether, methanol, ethanol, propyl alcohol, butanol, t-butyl methyl ether, acetone, chloroform and dichloromethane. The antisolvent used for the crystallization can be one or more among water, hexane, heptane, iso-octane and petroleum ether.

The following examples further illustrate the invention, it being understood that the invention is not intended to be limited by the details disclosed therein.

EXAMPLES

Example 1

Production of Tacrolimus by Fermentation of New *Streptomyces* sp.

One cryo-vial is aseptically transferred to a sterile 250-ml flask containing a sterile 50-ml of following Seed Medium:

| Ingredients | Concentration (g/L) |
| --- | --- |
| Soluble Starch | 10 |
| Glycerol | 10 |
| Dextrose Mono Hydrate (DMH) | 5 |
| Cotton Seed Flour (CSF) | 5 |
| Corn Steep Liquor (CSL) | 5 |
| Dried Yeast (DY) | 5 |
| CaCO3 | 2 | pH adjusted to 6.5+/−0.1 with NaOH

Medium sterilization was done at 121-123° C. for 45 minutes. Flask was incubated in a 28+/−1° C. shaker room at 230+/−10 rpm for a period of 48 log hr. Appreciable thickening of the broth after 36 h of incubation indicated good growth.

Sufficient seed for running a 20 L fermentor is generated by sub-culturing above seed in to a 2 L flask containing 350 ml of above mentioned seed medium. After a growth for 48 log hours, 170 ml of inoculum was transferred to 17 L of production medium sterilized at 121° C. for 1 h holding period in a 20 L fermentor.

Following production medium was employed for the experiment.

| Ingredients | Concentration(g/L) |
| --- | --- |
| Soluble Starch | 90 |
| Corn Steep Liquor | 10 |
| Dried Yeast | 20 |
| CaCO3 | 1 | pH adjusted to 6.8+/−0.1 with NaOH before sterilization.

Throughout the fermentation, pH was controlled at 6.8+−0.2 with sodium hydroxide or orthophosphoric acid.

Incubation temperature was controlled at 23+/−1° C. throughout the batch. Agitations, airflow, head pressure of fermentor were manipulated in order to control dissolved oxygen above 25%.

Samples were withdrawn every day for analysis of product content. Batch was continued till the activity stabilized in the broth. Final yield was 194 mg/L in 180 h with 15 mg/L of Ascomycin.

Example 2

Production of Tacrolimus by Fermentation of Mutant of New *Streptomyces* sp.

The mutant was obtained by classical UV mutation technique. Inoculum was developed in the same way as in the previous example. Production medium was used as given below.

| Ingredients | Concentration(g/L) |
| --- | --- |
| Soluble Starch | 99 |
| Corn Steep Liquor | 11 |
| Cotton Seed Flour | 2.5 |
| Dried Yeast | 20 |
| CaCO3 | 1 | pH adjusted to 6.8+/−0.1 with NaOH before sterilization.

Throughout the batch, pH was controlled at 6.8+/−0.2 with sodium hydroxide or orthophosphoric acid.

Incubation temperature was controlled at 23+/−1° C. throughout the batch. Agitations, airflow, head pressure of fermentor were manipulated in order to control dissolved oxygen above 25%.

On sixth day, a feed of following medium composition is prepared and added in such a way that volume of the fermentor broth increases by 10%.

| Ingredients | Concentration(g/L) |
| --- | --- |
| Dried yeast | 44 |
| Cotton seed flour | 27.5 |
| Starch | 200 |
| CaCO3 | 1 |

Samples were withdrawn every day for analysis of product content. Batch was harvested at 184 h and it gave a final activity of 254 mg/L with 25 mg/L of Ascomycin.

Example 3

Production of Tacrolimus by Fermentation of New *Streptomyces* sp.

Inoculum was developed in the same way as in the previous example. However, modified production medium was used as given below.

| Ingredients | Concentration(g/L) |
| --- | --- |
| Soluble Starch | 100 |
| (NH4)2SO4 | 3 |
| Corn Steep Liquor | 15 |
| Soya Flour | 5 |
| Cotton Seed Flour | 10 |
| Dried Yeast | 45 |
| CaCO3 | 1 | pH adjusted to 6.8+/−0.1 with NaOH before sterilization.

Throughout the batch, pH was controlled at 6.8+/−0.2 with sodium hydroxide or orthophosphoric acid.

Incubation temperature was controlled at 23+/−1° C. throughout the batch. Agitations, airflow, head pressure of fermentor were manipulated in order to control dissolved oxygen above 25%. Samples were withdrawn every day for analysis of product content.

Batch was harvested at 274 h and it gave a final activity of 337 mg/L with 30 mg/L of Ascomycin.

Example 4

Isolation and Purification of the Tacrolimus

The fermentation broth (30 Kg) containing 10 g Tacrolimus was extracted with 30 L of ethyl acetate. The ethyl acetate extract was partially concentrated to 2.4 L. The concentrate was chilled to 4° C. and ammonia was sparged through the concentrate for 30 minutes. The solution was filtered using celite as filter aid to separate the precipitated impurities. The filtrate was concentrated to obtain 82 g oily residue. The residue was applied on a silica gel column. The column was washed with 3 column volumes of 25% ethyl acetate in hexane and 3 column volumes of 50% ethyl acetate in hexane. The product was eluted with 75% ethyl acetate in hexane. The product containing fractions were pooled and concentrated to obtain 26 g oily residue. The residue was dissolved in 200 ml ethyl acetate. 27 g of activated charcoal was added to it. The mixture was stirred for 20 minutes and then filtered. The filtrate was concentrated to obtain 18 g of oily residue. To the residue, 5 ml of ethyl acetate was added. The crude product was crystallized at 4° C. by slow addition of hexane The crude product (6.2 g) was filtered and dried.

Example 5

Isolation and Purification of Tacrolimus 3.1 g of crude product obtained in example 4 was applied to a 3-L silica gel column. Silica gel (230-400 mesh) was initially treated with silver nitrate. The column was eluted with 75% ethyl acetate and 25% hexane. The product containing fractions with acceptable purity were pooled and concentrated. The product was crystallized as mentioned earlier from ethyl acetate and hexane. The crystals were filtered and dried. Substantially pure Tacrolimus was afforded by this method. The Ascomycin concentration in the final product was less than 0.2%.

Example 6

Isolation and Purification of the Tacrolimus 1. 3.1 g of crude product obtained in example 4 was applied to a C-8 reverse phase column (d~50 mm, L~210 mm). The product was eluted with acetonitrile:n-butanol:buffer in the ratio of 12.5:10:77.5. The buffer contained 1.36 g/L of $KH_2PO_4$, 1 ml/L triethyl amine, 1 ml/L phosphoric acid. The product containing fractions with acceptable purity were pooled and extracted with equal volume of ethyl acetate. The extract was washed with water, dried with sodium sulfate and concentrated. The product was crystallized as mentioned earlier from ethyl acetate and hexane. The crystals were filtered and dried. Substantially pure Tacrolimus was afforded by this method. The Ascomycin concentration in the final product was less than 0.1%.

We claim:
1. An isolated of *Streptomyces* sp. BICC 7522.

* * * * *

UNITED STATES PATENT AND TRADEMARK OFFICE
CERTIFICATE OF CORRECTION

PATENT NO. : 7,704,725 B2
APPLICATION NO. : 11/578108
DATED : April 27, 2010
INVENTOR(S) : Madhav Kulkarni et al.

It is certified that error appears in the above-identified patent and that said Letters Patent is hereby corrected as shown below:

In the specification, at Column 1, line 4, underneath the title, the Cross Reference to Related Applications is missing. Please add the following:

CROSS REFERENCE TO RELATED APPLICATIONS

This application claims priority to and the benefit of International Application Number PCT/IN2004/000099, filed April 12, 2004, and published as WO 2005/098011 A1 on October 20, 2005, which application is incorporated herein by reference in its entirety.

In the specification, at Column 1, line 29, please delete "p," and replace with --p.--.

In the specification, at Column 3, line 13, please delete "7522" and replace with --7522.--.

In the specification, at Column 3, line 67, please delete "Incubated" and replace with --incubated--.

In the specification, at Column 5, line 14, please move the entire line "pH adjusted to 6.5+/-0.1 with NaOH" up so that it appears underneath line 11 (line beginning "CaCO3") inside the table and above the solid line at the end of the table at line 12.

Signed and Sealed this

Seventh Day of December, 2010

David J. Kappos
*Director of the United States Patent and Trademark Office*

In the specification, at Column 5, line 37, please move the entire line "pH adjusted to 6.8+/-0.1 with NaOH before sterilization." up so that it appears underneath line 34 (line beginning "CaCO3") inside the table and above the solid line at the end of the table at line 35.

In the specification, at Column 5, line 38, please delete "+-" and replace with --+/- --.

In the specification, at Column 6, line 1, please move the entire line "pH adjusted to 6.8+/-0.1 with NaOH before sterilization." so that it appears underneath Column 5, line 65 (line beginning "CaCO3") inside the table and above the solid line at the end of the table at line 66.

In the specification, at Column 6, line 44, please move "pH adjusted to 6.8+/-0.1 with NaOH before sterilization." up so that it appears underneath Column 6, line 41 (line beginning "CaCO3") inside the table and above the solid line at the end of the table at line 42.

In the specification, at Column 8, line 8, please delete "1.3.1 g" and replace with --1.   3.1 g--.